(12) United States Patent
Rice (10) Patent No.: US 7,514,590 B1
(45) Date of Patent: *Apr. 7, 2009

(54) ISOMERIZATION PROCESS WITH ADSORPTIVE SEPARATION

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 880 days.

This patent is subject to a terminal disclaimer.

(21) Appl. No.: 11/078,994

(22) Filed: Mar. 11, 2005

(51) Int. Cl.
    *C07C 5/27* (2006.01)
(52) U.S. Cl. .................. 585/738; 585/734
(58) Field of Classification Search .......... 585/734, 585/738
See application file for complete search history.

(56) References Cited

U.S. PATENT DOCUMENTS

| | | | | |
|---|---|---|---|---|
| 2,966,528 | A | 12/1960 | Haensel | 260/666 |
| 3,755,144 | A | 8/1973 | Asselin | 208/95 |
| 4,709,116 | A | 11/1987 | Zarchy et al. | 585/738 |
| 4,709,117 | A | 11/1987 | Gray, Jr. | 585/738 |
| 4,717,784 | A | 1/1988 | Stem et al. | 585/738 |
| 4,804,802 | A | 2/1989 | Evans et al. | 585/734 |
| 4,831,209 | A | 5/1989 | Kruse | 585/738 |
| 5,026,951 | A | 6/1991 | Schmidt et al. | 585/738 |
| 5,043,525 | A | 8/1991 | Haizmann et al. | 585/737 |
| 5,146,037 | A | 9/1992 | Zarchy et al. | 585/738 |
| 5,326,926 | A | 7/1994 | Rice | 585/738 |
| 5,602,291 | A | 2/1997 | Minkkinen et al. | 585/738 |
| 5,705,730 | A | 1/1998 | Zarchy et al. | 585/738 |
| 6,069,289 | A * | 5/2000 | Dandekar et al. | 585/820 |
| 6,706,659 | B2 * | 3/2004 | Gillespie et al. | 502/217 |
| 7,223,898 | B2 * | 5/2007 | Rice | 585/738 |

OTHER PUBLICATIONS

Handbook of Petroleum Refining Processes, Robert A. Meyers, McGraw-Hill Book Company, 1986, pp. 5-49 through 5-51.

* cited by examiner

*Primary Examiner*—In Suk Bullock
(74) *Attorney, Agent, or Firm*—Maryann Maas (57) ABSTRACT

Isomerization of a feedstream comprising $C_5$ to $C_6$ hydrocarbons involving charging hydrogen and the feedstream into an isomerization zone to contact an isomerization catalyst at isomerization conditions and increase the branching of the feedstream hydrocarbons to produce an isomerization effluent stream has been discovered. Without passing through a stabilizer, the isomerization effluent is passed through a product separator and a flash drum and then to an adsorptive separation zone to generate a raffinate stream enriched in branched alkanes, an extract stream enriched in normal alkanes, and at least one light ends stream. Within the adsorptive separation zone, the raffinate and the extract streams are each passed through a fractionator remove light ends and desorbent. The desorbent is recycled to the adsorptive separation zone. The remainder of the extract stream is recycled to the isomerization zone and the remainder of the raffinate stream is collected.

20 Claims, 2 Drawing Sheets

ISOMERIZATION PROCESS WITH ADSORPTIVE SEPARATION

FIELD OF THE INVENTION

This invention relates generally to the isomerization of hydrocarbons. This invention relates more specifically to the isomerization of light paraffins using a solid catalyst, and the separation of more highly branched paraffins from less highly branched paraffins by adsorptive separation.

BACKGROUND OF THE INVENTION

High octane gasoline is required for modern gasoline engines. Formerly it was common to accomplish octane number improvement by the use of various lead-containing additives. As lead was phased out of gasoline for environmental reasons, octane ratings were maintained with other aromatic and low vapor pressure hydrocarbons. Environmental damage caused by the vaporization of low vapor pressure hydrocarbons and the health hazards of benzene in motor fuel will lead to further restrictions on octane blending components. Therefore, it has become increasingly necessary to rearrange the structure of the $C_5$ and $C_6$ hydrocarbons used in gasoline blending in order to obtain high octane levels. Catalytic isomerization is a widely used process for this upgrading.

The traditional gasoline blending pool normally includes $C_4$ and heavier hydrocarbons having boiling points of less than 205° C. (395° F.) at atmospheric pressure. This range of hydrocarbon includes $C_4$ to $C_6$ paraffins and especially the $C_5$ and $C_6$ normal paraffins which have relatively low octane numbers. The $C_4$ to $C_6$ hydrocarbons have the greatest susceptibility to octane improvement by lead addition and were formerly upgraded in this manner. With eventual phase out of lead additives octane improvement was obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branched-chain isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Moreover, the health concerns related to benzene are likely to generate overall restrictions on benzene and possibly aromatics as well, which some view as precursors for benzene tail pipe emissions. Therefore, it is preferred to change the $C_6$ paraffins to an isomerization unit to obtain $C_6$ isoparaffin hydrocarbons. Consequently, octane upgrading commonly uses isomerization to convert $C_6$ and lighter boiling hydrocarbons.

The effluent from an isomerization reaction zone will contain a mixture of more highly branched and less highly branched paraffins, hydrogen and light ends containing from one to four carbon atoms. Hydrogen is removed in a product separator unit and recycled to the isomerization reactor. The light ends are removed from the desired isomerized products in a stabilizer. In order to further increase the octane of the products from the isomerization zone, normal paraffins, and sometimes less highly branched isoparaffins, are typically recycled to the isomerization zone along with the feedstream in order to increase the ratio of less highly branched paraffins to more highly branched paraffins entering the isomerization zone. A variety of methods are known to treat the effluent from the isomerization zone for the recovery of normal paraffins and monomethyl-branched isoparaffins for recycling these less highly branched paraffins to the isomerization zone.

Relatively higher octane isomers are commonly separated from lower octane normal paraffins and monomethyl-branched paraffins by using a distillation zone, adsorptive separation or some combination thereof. General arrangements for the separation and recycling of $C_5$ and $C_6$ hydrocarbons in isomerization units are shown and described at pages 549 through 5-51 of THE HANDBOOK OF PETROLEUM REFINING PROCESSES, edited by Robert A. Meyers, published by McGraw Hill Book Company (1986). Distillation is a primary method of recovering the desired higher octane isomers from the lower octane isomers with the lower octane isomers potentially being recycled to the isomerization zone.

Similarly, another technique for separating the high octane isomers from the lower octane isomers is adsorptive separation under liquid phase conditions. In such methods, the isomerization effluent contacts a solid adsorbent having a selectivity for normal paraffins to effect the selective adsorption of normal paraffins and allow recovery of the isoparaffins as a high octane product. Contacting the normal paraffin containing adsorbent with the desorbent material in a desorption step removes normal paraffins from the adsorbent for recycle to the isomerization zone. Both the isoparaffin and normal paraffin containing streams undergo a separation for the recovery of desorbent before the isoparaffins are recovered as a product and the normal paraffins recycled to the isomerization zone. Liquid phase adsorption has been carried out in conventional swing bed systems as shown in U.S. Pat. No. 2,966,528. The use of simulated moving bed systems for the selective adsorption of normal paraffins is also known and disclosed by U.S. Pat. No. 3,755,144. Simulated moving bed systems have the advantage of increasing recovery and purity of the adsorbed and non-adsorbed components in the isomerization zone effluent for a given unit of adsorbent material.

Adsorption processes using vapor phase adsorption for the separation of normal and branched paraffins are also well known. Examples of such processes are described in U.S. Pat. No. 4,709,116 and U.S. Pat. No. 4,709,117. These references teach the use of multiple adsorbent vessels and the steps of adsorbing and desorbing the normal paraffins from an isomerization zone effluent. In addition, one or more steps of blow-down or void space purging are also taught to increase the recovery of product hydrocarbons.

Recent efforts in adsorptive separation teach adsorbents and flow schemes for also separating monomethyl paraffins from dimethyl-branched paraffins. U.S. Pat. No. 4,717,784 and U.S. Pat. No. 4,804,802 disclose processes for the isomerization of a hydrocarbon feed and the use of multiple adsorptive separations to generate normal paraffin and monomethyl-branched paraffin recycle streams. In such systems the effluent from the isomerization zone enters a molecular sieve separation zone that contains a 5 A-type sieve and a ferrierite-type sieve that adsorb normal paraffins and monomethyl-branched paraffins, respectively. U.S. Pat. No. 4,804,802 discloses steam or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

Another method of recovering the high octane isomers from lower octane isomers and normal paraffins uses adsorptive separation followed by distillation. U.S. Pat. No. 3,755,144 shows a process for the isomerization of a pentane/hexane feed and the separation of normal paraffins from the isomerization zone effluent. The isomerization zone effluent is separated by a molecular sieve separation zone that includes facilities for the recovery of desorbent from the normal paraffin containing stream that is recycled to the isomerization zone. An extract stream that contains isoparaffins is sent to a deisohexanizer column that separates isopentane and dimethylbutane as a product stream and provides a recycle stream of isohexane that is returned to the isomerization zone. U.S. Pat. No. 5,043,525 teaches eliminating the fractionation columns typically used to separate desorbent from streams exiting an adsorptive separation zone. U.S. Pat. No. 5,602,291 teaches using pressure swing adsorption to separate isomerization effluent. U.S. Pat. No. 2,966,528, discloses a process for the isomerization of $C_6$ hydrocarbons and the adsorptive separation of normal hydrocarbons from branched-chain hydrocarbons.

The present invention involves an isomerization process that eliminates a commonly employed unit. Specifically, the present invention eliminates the need for a stabilizer column to separate the light ends from the desired isomerized products. Stabilizer columns have been traditionally used in isomerization processes, see U.S. Pat. No. 5,026,951, U.S. Pat. No. 5,146,037, U.S. Pat. No. 4,831,209, U.S. Pat. No. 5,705,730 and U.S. Pat. No. 5,326,926. In the present invention however, the effluent of the isomerization reactor is passed to a product separator to remove and recycle hydrogen, and then to an adsorptive separation zone. In the separation zone unadsorbed hydrocarbons are recovered as high octane product, and straight-chain hydrocarbons having a lower octane value are desorbed using a normal paraffin desorbent. The straight-chain hydrocarbons are recycled to the isomerization zone. The costly stabilizer column is eliminated and the function of the stabilizer is accomplished by the flash drum and the separation zone of the invention. The present invention provides an isomerization process having lower capital costs and lower utilities costs due to the elimination of the stabilizer column.

SUMMARY OF THE INVENTION

The invention is a process for the isomerization of a feedstream comprising $C_5$ to $C_6$ hydrocarbons where the process involves charging hydrogen and a feedstream comprising at least normal $C_5$ to $C_6$ hydrocarbons into an isomerization zone and contacting said hydrogen and feedstream with a solid acid isomerization catalyst at isomerization conditions to increase the branching of the feedstream hydrocarbons and produce an isomerization effluent stream comprising at least normal pentane, normal hexane, methylbutane, dimethylbutane, and methylpentane. The isomerization effluent stream to a product separator to separate a hydrogen-rich stream from an isomerized product stream. A flash drum is used to separate the light ends. The remainder of the isomerized product stream is passed to an adsorptive separation zone to separate a butane and light ends stream, a raffinate isomerate product stream containing higher octane isomers, an extract recycle stream containing lower octane isomers, and a heavy hydrocarbon stream containing cyclohexane and hydrocarbons having seven or more carbon atoms.

DETAILED DESCRIPTION OF THE INVENTION

Applicants have discovered that the isomerization of a feedstock containing $C_5$ and $C_6$ hydrocarbons can be successfully achieved in a less costly flowscheme than that currently in use in industry. Specifically, in an isomerization process using a solid catalyst, the traditional stabilizer column may be eliminated and the separation of light ends from isomerized products, usually performed by the stabilizer column instead may be accomplished by a combination of a flash drum and the adsorptive separation zone. Optionally, lower octane methylpentanes and normal hexane may be recycled to the isomerization zone to increase the octane number. In general, a feedstock comprising $C_5$ to $C_6$ hydrocarbons is contacted with an isomerization catalyst in an isomerization zone at isomerization conditions and thereby increases the branching of the feedstream hydrocarbons and produces an isomerization zone effluent stream that comprises at least hydrogen, normal pentane, normal hexane, methylbutane, dimethylbutane and methylpentane, naphthenes, and light ends. The effluent from the isomerization zone passes first to a product separator to remove and optionally recycle hydrogen. The bottoms of the product separator which contains the isomerized products and light ends are conducted to a product separator, then to a flash drum and finally to a separation zone. The light ends, a recycle stream, a $C_7^+$ stream and an isomerized product stream are all separated in the separation zone.

The feedstocks that can be used in this invention include hydrocarbon fractions rich in $C_4$ to $C_6$ normal paraffins. The term "rich" is defined to mean a stream having more than 50% of the mentioned components. Preferred feedstocks are substantially pure normal paraffin streams having from 4 to 6 carbon atoms or a mixture of such substantially pure normal paraffins. Other useful feedstocks include light natural gasoline, light straight run naphtha, gas oil condensate, light raffinates, light reformate, light hydrocarbons, field butanes, and straight run distillates having distillation end points of about 77° C. (170° F.) and containing substantial quantities of $C_4$ to $C_6$ paraffins. The feed stream may also contain low concentrations of unsaturated hydrocarbons and hydrocarbons having more than 6 carbon atoms.

Hydrogen is admixed with the feed in an amount that will provide a hydrogen to hydrocarbon ratio equal to or less than 0.10 in the effluent from the isomerization zone when operating without hydrogen recycle. The hydrogen to hydrocarbon ratio of 0.10 or less at the effluent has been found to provide sufficient excess hydrogen for operation of the process. Although no net hydrogen is consumed in the isomerization reaction, the isomerization zone will have a net consumption of hydrogen often referred to as the stoichiometric hydrogen requirement which is associated with a number of side reactions that occur. These side reactions include cracking and disproportionation. Other reactors that will also consume hydrogen include olefin and aromatics saturation. For feeds having a low level of unsaturates, satisfying the stoichiometric hydrogen requirements demand a hydrogen to hydrocarbon molar ratio for the outlet stream of between 0.01 to 10.0. Hydrogen in excess of the stoichiometric amounts for the side reactions is maintained in the reaction zone to provide good stability and conversion by compensating for variations in feed stream compositions that alter the stoichiometric hydrogen requirements.

When the hydrogen to hydrocarbon ratio exceeds 0.10, it is not economically desirable to operate the isomerization process without the recycle of hydrogen to the isomerization zone. As the quantity of hydrogen leaving the product recovery section increases, additional amounts of $C_4$ and other product hydrocarbons are taken by the fuel gas stream from the product recovery section. The value of the lost product or the additional expense associated with recovery facilities to prevent the loss of product do not justify operating the process without recycle at hydrogen to hydrocarbon ratios above 0.10. However, when employing hydrogen recycle, hydrogen is admixed with the feed in an amount that will provide a hydrogen to hydrocarbon ratio equal to from 0.01 to about 10.0 in the effluent from the isomerization zone.

Hydrogen may be added to the feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in the outlet stream or one of the outlet stream fractions is monitored by a hydrogen monitor and the control valve setting position is adjusted to maintain the desired hydrogen concentration. The hydrogen concentration at the effluent is calculated on the basis of total effluent flow rates.

The hydrogen and hydrocarbon feed mixture is contacted in the isomerization zone with a solid isomerization catalyst. The catalyst composites that can be used in the isomerization zone include traditional isomerization catalysts including solid strong acid catalysts and crystalline aluminosilicates or zeolites. Suitable catalyst compositions of this type will exhibit selective and substantial isomerization activity under the operating conditions of the process.

As a class, the crystalline aluminosilicate or crystalline zeolite catalysts comprise crystalline zeolitic molecular sieves having an apparent pore diameter large enough to adsorb neopentane. A silica alumina molar ratio $SiO_2:Al_2O_3$ of greater than 3; less than 60 and preferably between 15 and 30 is desirable. In preferred form, the zeolite will contain an equivalent percentage of alkali metal cations and will have those $AlO_4$-tetrahedra not associated with alkali metal cations, either not associated with any metal cations or associated with divalent or other polyvalent metal cations. Usually the molecular sieve is a mordenite molecular sieve, which is essentially in the acid form or is converted to the acid form. Catalysts of this type for isomerization are disclosed in detail in U.S. Pat. No. 3,442,794 and U.S. Pat. No. 3,836,597 which are hereby incorporated by reference.

A composition of zeolitic catalyst for use in the present invention comprises a Group VIII noble metal, a hydrogen form crystalline aluminosilicate, and a refractory inorganic oxide with the catalyst composition having a surface area of at least 580 $m^2/g$. Significant improvements in isomerization performance are realized when the surface area of the catalytic composite is at or above 580 $m^2/g$. A Group VIII metal is incorporated into the catalytic composite to supply a hydrogenation/dehydrogenation function such as the Group VIII noble metal platinum. The Group VIII noble metal is present in an amount from about 0.01 to 5% by weight of the composite or in an amount of at least 0.15% by weight but not over 0.35% by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are suitable, particularly with a silica to alumina ratio of at least 16:1. The hydrogen form aluminosilicate may be present in an amount within the range of 50 to about 99.5 wt-%, or within the range of 75 to about 95 wt-%, and a refractory inorganic oxide may be present in an amount within the range of from 25 to about 50 wt-%.

Another suitable solid strong acid isomerization catalyst comprises a sulfated support of an oxide or hydroxide of a Group IVB (IUPAC 4) metal, such as zirconium oxide or hydroxide, at least a first component which is a lanthanide element or yttrium component, and at least a second component being a platinum-group metal component. The catalyst optionally contains an inorganic-oxide binder, especially alumina. The catalyst is fully described in U.S. Pat. No. 6,706,659 which is hereby incorporated by reference in its entirety. Sulfated zirconia is also an acceptable catalyst.

The support material of the catalyst of the present invention comprises an oxide or hydroxide of a Group IVB (IUPAC 4). In one embodiment the Group IVB element is zirconium or titanium. Sulfate is composited on the support material. A component of a lanthanide-series element is incorporated into the composite by any suitable means. The lanthanide series element component may be selected from the group consisting of lanthanum, cerium, praseodymium, neodymium, promethium, samarium, europium, gadolinium, terbium, dysprosium, holmium, erbium, thulium, ytterbium and lutetium. Suitable amounts of the lanthanide series element component are in the range of about 0.01 to about 10 mass-% on an elemental basis, of the catalyst. A platinum-group metal component is added to the catalytic composite by any means known in the art to effect the catalyst of the invention, e.g., by impregnation. The platinum-group metal component may be selected from the group consisting of platinum, palladium, ruthenium, rhodium, iridium, or osmium. Amounts in the range of from about 0.01 to about 2 wt-% platinum-group metal component, on an elemental basis are suitable.

Optionally, the catalyst is bound with a refractory inorganic oxide. The binder, when employed, usually comprises from about 0.1 to 50 mass-%, or from about 5 to 20 mass-%, of the finished catalyst. The support, sulfate, metal components and optional binder may be composited in any order effective to prepare a catalyst useful for the isomerization of hydrocarbons. An atomic ratio of lanthanide or yttrium to platinum-group metal for this catalyst is at least about 1:1, or about 2:1 or greater, and especially about 5:1 or greater. The catalyst may optionally further include a third component of iron, cobalt, nickel, rhenium or mixtures thereof. For example, iron may be present in amounts ranging from about 0.1 to about 5 wt-% on an elemental basis. Production of the catalyst is described in U.S. Pat. No. 6,706,659 B1 which is incorporated by reference in its entirety and not reproduced here.

Operating conditions within the isomerization zone are selected to maximize the production of isoalkane product from the feed components. Temperatures within the reaction zone will usually range from about 40° to about 235° C. (100° to 455° F.). Lower reaction temperatures are generally preferred since they usually favor equilibrium mixtures of branched alkanes versus normal alkanes. Lower temperatures are particularly useful in processing feeds composed of $C_5$ and $C_6$ alkanes where the lower temperatures favor equilibrium mixtures having the highest concentration of the most branched alkanes. When the feed mixture is primarily $C_5$ and $C_6$ alkanes temperatures in the range of from 60° to 160° C. are suitable. Thus, when the feed mixture contains significant portions of $C_4$ to $C_6$ alkanes most suitable operating temperatures are in the range from 145° to 225° C. The reaction zone may be maintained over a wide range of pressures. Pressure conditions in the isomerization of $C_4$ to $C_6$ paraffins range from 700 to 7000 kPa (abs). Suitable pressures for this process are in the range of from 2000 to 3000 kPa (abs). The feed rate to the reaction zone can also vary over a wide range. These conditions include liquid hourly space velocities ranging from 0.5 to 12 hr$^{-1}$ or between 1 and 6 hr$^{-1}$.

The effluent of the isomerization is processed to separate the desired isomerized products from hydrogen, light ends, lower octane isomerized products, and cyclohexane plus heavy hydrocarbons having 7 or more carbon atoms. The flow scheme does not require a stabilizer column to separate the light ends from the isomerized products. A product separator is used to remove hydrogen and gasses and a flash drum is used to further remove light ends such as propane and lighter materials. Conditions for the operation of the product separator include pressures ranging from 689 to 4137 kPa (abs) (100 to 600 psia). Specific embodiments utilize pressures from 1379 to 3447 kPa (abs) (200 to about 500 psia). Suitable designs for rectification columns and separator vessels suitable for use as the product separator are well known to those skilled in the art.

The hydrogen depleted isomerization effluent is then directed to a flash drum. Using a flash drum is significantly less costly than a stabilizer. The flash drum is operated at 0 to 1483 kPa (abs) (0 to 215 psia) or 345 to 793 kPa (abs) (50 to 115 psia) and separates a flash drum overhead containing $C_3$ and lighter hydrocarbons and gasses such as propane, ethane, methane, and hydrogen from a flash drum bottoms containing butane and heavier hydrocarbons. The flash drum bottoms is also expected to contain up to about 10 wt-% or up to about 5 wt-% of $C_3$ and lighter hydrocarbons and gasses such as propane, ethane, methane, and hydrogen. The separation performed in the flash drum need not be precise, and it is acceptable for some of the lighter components to be present in the flash drum bottoms stream.

Specifically, after the product separator has removed hydrogen and light gasses, and after the flash drum has removed propane and lighter materials, the remainder of the isomerization zone effluent will comprise butane and lower boiling hydrocarbons and is taken from the flash drum and transferred to the adsorptive separation zone. The adsorptive separation zone is used to separate and recycle the normal alkanes and to separate the desired branched isomerized products. In addition, the butane and lighter hydrocarbons and gasses are separated and removed, a function that previously required a stabilizer column. The most desired isomerization zone products are recovered from the adsorptive separation zone in the raffinate product stream.

The adsorption zone is operated in the liquid phase and can utilize any type of well known adsorption process such as a swing bed, simulated moving bed, or other schemes for contacting the adsorbent with the feed mixture and desorbing the feed mixture from the adsorbent with the desorbent material. A simulated moving bed type adsorption system has been found to be most useful for this process. The adsorptive separation zone provides the normal alkane stream which is recycled to the isomerization zone. A product stream comprising methylbutane and dimethylbutanes are recovered as the raffinate or non-adsorbed components from the adsorptive separation zone.

Virtually any adsorbent material that has capacity for the selective adsorption of the normal paraffin components can be used in the adsorptive separation section. Suitable adsorbents known in the art and commercially available include crystalline molecular sieves, activated carbons, activated clays, silica gels, activated aluminas and the like. The molecular sieves include, for example, the various forms of silicoaluminophosphates and aluminophosphates disclosed in U.S. Pat. No. 4,440,871; U.S. Pat. No. 4,310,440 and U.S. Pat. No. 4,567,027, hereby incorporated by reference, as well as zeolitic molecular sieves. Zeolitic molecular sieves in the calcined form may be represented by the general formula; $Me_{2/n}O:Al_2O_3:xSiO:yH_2O$, where Me is a cation, x has a value from about 2 to infinity, n is the cation valence and y has a value of from about 2 to 10.

Typical well-known zeolites which may be used include, chabazite, also referred to as Zeolite D, clinoptilolite, erionite, faujasite, also referred to as Zeolite X and Zeolite Y, ferrierite, mordenite, Zeolite A, and Zeolite P. Other zeolites suitable for use according to the present invention are those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above-identified zeolites may be found in D. W. Breck, ZEOLITE MOLECULAR SIEVES, John Wiley and Sons, New York, 1974, hereby incorporated by reference. Adsorbents for a PSA type adsorption section include a type 5 A molecular sieve in the form of ⅛ pellets. The selection of other adsorbents for normal hydrocarbon separation can be made by one skilled in the art with routine experimentation.

Additional adsorbents capable of selectively adsorbing the branched paraffins and rejecting the normal paraffins are aluminophosphates from the group comprising SAPO-5, AlPO$_4$-5, and MAPSO-5, and MgAPO-5 and SSZ-24 (an all-silica molecular sieve that is isostructural with AlPO$_4$-5). SAPO-5 is a silicoaluminophosphate whose method of manufacture, structure and properties are disclosed in U.S. Pat. No. 4,440,871. AlPO$_4$-5 is an aluminophosphate having a pore size of 8 Å and may be made by the method disclosed in U.S. Pat. No. 4,310,440. MgAPO-5 is a metalloaluminophosphate having the structural formula, properties and method of manufacture disclosed in U.S. Pat. No. 4,567,029. As described in U.S. Pat. No. 4,310,440, MAPSO-5 is a metallosilica aluminophosphate in which the metal is magnesium and whose structural formula, properties and method of manufacture are disclosed in U.S. Pat. No. 4,758,419. SSZ-24 is isostructural with AlPO$_4$-5 and is described in U.S. Pat. No. 4,834,958.

Typically, adsorbents used in separation processes, such as described herein, contain the crystalline material dispersed in an amorphous inorganic matrix or binder, having channels and cavities therein which enable liquid access to the crystalline material. Although there are a variety of synthetic and naturally occurring binder materials available such as metal oxides, clays, silicas, aluminas, silica-aluminas, silica-zirconias, silica thorias, silica-berylias, silica-titanias, silica-aluminas-thorias, silica-alumina-zirconias, mixtures of these and the like, clay-type binders are suitable. Examples of clays which may be employed to agglomerate the molecular sieve without substantially altering the adsorptive properties of the zeolite are attapulgite, kaolin, volclay, sepiolite, polygorskite, kaolinite, bentonite, montmorillonite, illite and chlorite. The binder, typically in amounts ranging from 2 to 25% by weight, aids in forming or agglomerating the crystalline particles of the zeolite which otherwise would comprise a fine powder. The adsorbent may thus be in the form of particles such as extrudates, aggregates, tablets, macrospheres or granules having a desired particle size range, from about 16 to 40 mesh (Standard U.S. Mesh) (1 mm to 420 microns). The choice of a suitable binder and methods employed to agglomerate the molecular sieves are generally known to those skilled in the art.

In the moving bed or simulated moving bed processes, the retention and displacement operations are continuously taking place which allows both continuous production of an extract and a raffinate stream and the continuous use of feed and displacement fluid streams. The operating principles and sequence of the simulated moving bed countercurrent flow system are described in U.S. Pat. No. 2,985,589 incorporated herein by reference in its entirety. In such a system, it is the progressive movement of multiple liquid access points down a adsorbent chamber that simulates the upward movement of adsorbent contained in the chamber.

A number of specially defined terms are used in describing the simulated moving bed processes. The term "feed stream" indicates a stream in the process through which feed material passes to the adsorbent. A feed material comprises one or more extract components and one or more raffinate components. An "extract component" is a compound or type of compound that is more selectively retained by the adsorbent while a "raffinate component" is a compound or type of compound that is less selectively retained. In this process, branched hydrocarbons from the feed stream are raffinate components while feed stream normal hydrocarbons are extract components. The term "displacement fluid" or "desorbent" shall mean generally a material capable of displacing an extract component. The term "desorbent input stream" indicates the stream through which desorbent passes to the molecular sieve. The term "raffinate output stream" means a stream through which most of the raffinate components are removed from the molecular sieve. The composition of the raffinate stream can vary from about 100% desorbent to essentially 100% raffinate components. The term "extract stream" or "extract output stream" shall mean a stream through which an extract material which has been displaced by desorbent is removed from the molecular sieve. The composition of the extract stream can also vary from about 100% desorbent to essentially 100% extract components.

The term "selective pore volume" of the adsorbent is defined as the volume of the adsorbent which selectively retains extract components from the feedstock. The term "non-selective void volume" of the adsorbent is the volume of the adsorbent which does not selectively retain extract components from the feedstock. This volume includes the cavities of the adsorbent which are capable of retaining raffinate components and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of molecular sieve.

When adsorbent "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the molecular sieve. Since this net entrainment is a fluid present in a non-selective void volume of the molecular sieve, it, in most instances, comprises less selectively retained feed components.

In a simulated moving bed process only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of molecular sieve. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones be present in order for the process to take place although in some instances an optional fourth zone may be used.

The adsorption zone, zone I, is defined as the adsorbent located between the feed inlet stream and the raffinate outlet stream. In this zone, the feedstock contacts the molecular sieve, an extract component is retained, and a raffinate stream is withdrawn. Since the general flow through zone I is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in adsorption zone I is the purification zone II. The purification zone II is defined as the adsorbent between the extract outlet stream and the feed inlet stream. The basic operations taking place in zone II are the displacement from the non-selective void volume of the adsorbent of any raffinate material carried into zone II by the shifting of adsorbent into this zone and the displacement of any raffinate material retained within the selective pore volume of the molecular sieve. Purification is achieved by passing a portion of extract stream material leaving zone III into zone II at zone II's upstream boundary to effect the displacement of raffinate material. The flow of liquid in zone II is in a downstream direction from the extract outlet stream to the feed inlet stream.

Immediately upstream of zone II with respect to the fluid flowing in zone II is the desorption zone II. The desorption zone III is defined as the adsorbent between the desorbent inlet and the extract outlet streams. The function of the desorption zone is to allow a desorbent which passes into this zone to displace the extract component which was retained in the adsorbent during a previous contact with feed in zone I in a prior cycle of operation. The flow of fluid in zone III is essentially in the same direction as that of zones I and II.

In some instances, an optional buffer zone, zone IV, may be utilized. This zone, defined as the adsorbent between the raffinate outlet stream and the desorbent inlet stream, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent present in that zone out of the zone into the desorption zone. Zone IV will contain enough desorbent so that raffinate material present in the raffinate stream passing out of zone I and into zone IV can be prevented from passing into zone III thereby contaminating extract stream removed from zone II. In the instances in which the fourth operational zone is not utilized, the raffinate stream passed from zone I to zone IV must be carefully monitored in order that the flow directly from zone I to zone III can be stopped when there is an appreciable quantity of raffinate material present in the raffinate stream passing from zone I into zone III so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. No. 3,040,777 and U.S. Pat. No. 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations, the buffer zone can contain a minor amount of adsorbent as compared to the adsorbent required for the adsorption and purification zones. It can also be seen that in instances in which desorbent is used which can easily displace extract material from the adsorbent that a relatively small amount of adsorbent will be needed in the desorption zone as compared to the adsorbent needed in the adsorption zone or purification zone. Since it is not required that the adsorbent be located in a single column, the use of multiple chambers or a series of columns is within the scope of the invention.

It is not necessary that all of the input or output streams be simultaneously used, and, in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

In the typical operation of this process, at least a portion of the raffinate output stream and a portion of the extract output stream will be passed to a separation means wherein at least a portion of the desorbent can be separated to produce a desorbent stream which can be reused in the process and raffinate and extract products containing a reduced concentration of desorbent. The separation means will typically be a fractionation column, the design and operation of which is well known to the separation art.

Although both liquid and vapor phase operations can be used in many adsorptive type separation processes, liquid-phase operation is preferred for this process because of the lower temperature requirements and because of the higher yields of extract product that can be obtained with liquid-phase operation over those obtained with vapor-phase operation. Adsorption conditions will, therefore, include a pressure sufficient to maintain liquid phase. Adsorption conditions will include a temperature range of from about 60° to about 200° C., or about 100° to about 180° C. and a pressure sufficient to maintain liquid-phase, ranging from about atmospheric to about 3551 kPa (abs) (515 psia) with from about atmospheric to about 1482 kPa (abs) (215 psia) usually being adequate. Desorption conditions will include the same range of temperatures and pressures as used for adsorption conditions.

In general, a desorbent must be selected to satisfy the following criteria. First, the desorbent material should displace an extract component from the adsorbent with reasonable mass flow rates without itself being so strongly adsorbed in the following adsorption cycle. Second, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. In one embodiment of the invention, the raffinate stream and the extract stream from the rotary valve of the simulated moving bed system are directed to fractionation columns to separate and recycle the desorbent. Finally, desorbent materials should also be materials which are readily available and reasonable in cost. Examples of desorbents used in isothermal, isobaric, liquid-phase operations include $C_4$ to $C_6$ n-paraffins, e.g., n-butane, n-pentane, and n-hexane. The desorbent stream may, in addition to the desorbent, contain up to 30 wt-% or up to 5 wt-% non normals such as branched alkanes and aromatics.

Without the commonly used stabilizer, the extract stream and the raffinate stream from the simulated moving bed system will also contain butanes and lighter hydrocarbons and gasses. These light ends are readily separated from other components in the raffinate and extract streams in several different ways. The fractionation column used to separate the desorbent could also be operated to separate the light ends. Another variation would be to separate the desorbent in the raffinate fractionation columns and the extract fractionation column, and passing the remaining extract stream and raffinate stream to an extract receiver and a raffinate receivers. In the light ends readily resolve into an overhead stream and the final extract and raffinate streams are withdrawn from the receivers as bottoms streams.

One embodiment of the invention is described with reference to FIG. 1. Reference to the specific arrangement for this invention is not meant to limit it to the details disclosed therein. Furthermore, FIG. 1 is a schematic illustration and does not show a number of details for the process arrangement such as pumps, compressors, valves, and recycle lines which are well known to those skilled in the art.

Figure 1:
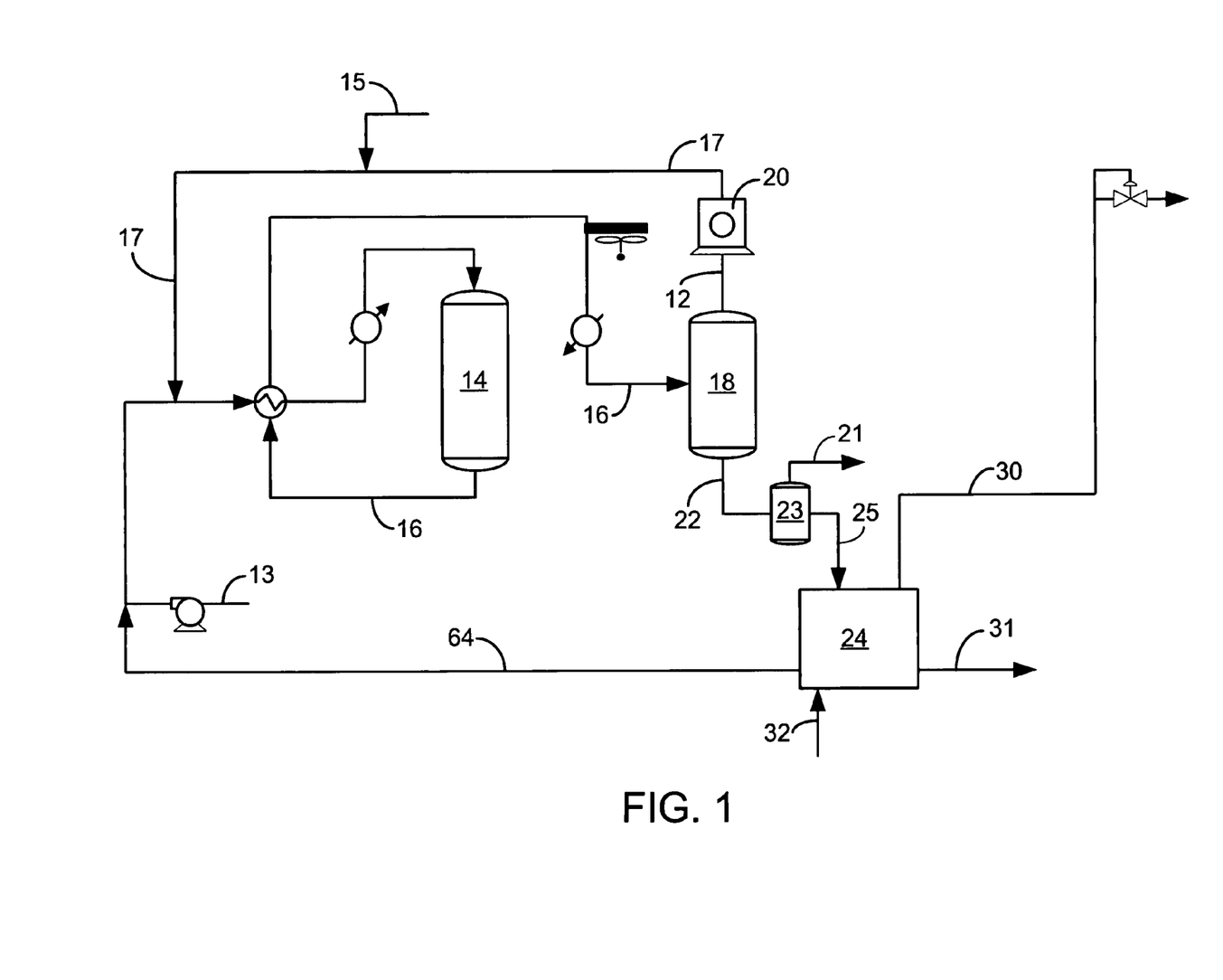
FIG. 1 is a schematic drawing of the process of this invention including the adsorptive separation zone.

FIG. 1 shows four primary operating zones, an isomerization zone, a product separator zone, a flash drum, and a fractionation separation zone. Fresh feed of the type previously described is introduced via line 13 to the isomerization zone 14 which contains solid isomerization catalyst. The isomerization zone is operated at conditions previously discussed. Hydrogen in line 17 is admixed with the feed to the isomerization zone in an amount that will provide a hydrogen to hydrocarbon molar ratio of from 0.01 to 10.0 in the effluent from the isomerization zone.

The isomerization zone 14 is shown as a single reactor system. The invention is not restricted to a particular type of isomerization zone. The isomerization zone can consist of any type of isomerization zone that takes a stream of $C_5$ to $C_6$ straight-chain hydrocarbons or a mixture of straight-chain and branched-chain hydrocarbons and converts straight-chain hydrocarbons in the feed mixture to branched-chain hydrocarbons and branched hydrocarbons to more highly branched hydrocarbons thereby producing an effluent having branched-chain and straight-chain hydrocarbons. A two-reactor system with a first stage reactor and a second stage reactor in the reaction zone is an alternative embodiment. For a two reactor system, the catalyst used is distributed between the two reactors in any reasonable distribution. It is not necessary that the reaction be carried out in two reactors but the use of two reactors confer several benefits on the process.

The effluent from the isomerization zone in line 16 enters a product separator 18 that divides the reaction zone effluent into a product stream 22 comprising $C_4$ and heavier hydrocarbons, and an overhead gas stream 17 which is made up of hydrogen and lighter hydrocarbons including $C_3$ and lighter boiling compounds. The isomerization zone effluent in line 16 may be heat exchanged with the feed stream 13 before being passed to product separator 18. Conditions for the operation of the product separator include pressures ranging from 689 to 4137 kPa (abs) (100 to 600 psia). Specific embodiments utilize pressures from 1379 to 3447 kPa (abs) (200 to about 500 psia). Suitable designs for rectification columns and separator vessels suitable for use as the product separator are well known to those skilled in the art. The product separator may optionally include a preheat loop from which the $C_4^+$ products stream is withdrawn (not shown). The hydrogen-rich gas stream is carried in line 17 from the product separator and is recycled using recycle compressor 20 to combine with feedstock in line 13. Additional hydrogen, if necessary, may be added through line 15. The products stream 22 from the product separator is passed to flash drum 23 and then to an adsorptive separation zone 24.

Traditionally, a stabilizer would be employed to remove light gases and butane from the products stream. In the present invention however, products stream 22 is directed to a less costly flash drum 23. Flash drum 23 is operated at 0 to 1483 kPa (abs) (0 to 215 psia) or 345 to 793 kPa (abs) (50 to 115 psia) and separates a flash drum overhead 21 from a flash drum bottoms 25. Flash drum overhead 21 contains $C_3$ and lighter hydrocarbons and gasses such as propane, ethane, methane, and hydrogen. Flash drum bottoms 25 contains butane and heavier hydrocarbons. Flash drum bottoms 25 is expected to also contain up to about 10 wt-% or up to about 5 wt-% of $C_3$ and lighter hydrocarbons and gasses such as propane, ethane, methane, and hydrogen. The separation performed in the flash drum need not be precise, and it is acceptable for some of the lighter components to be present in the flash drum bottoms stream.

Figure 2:
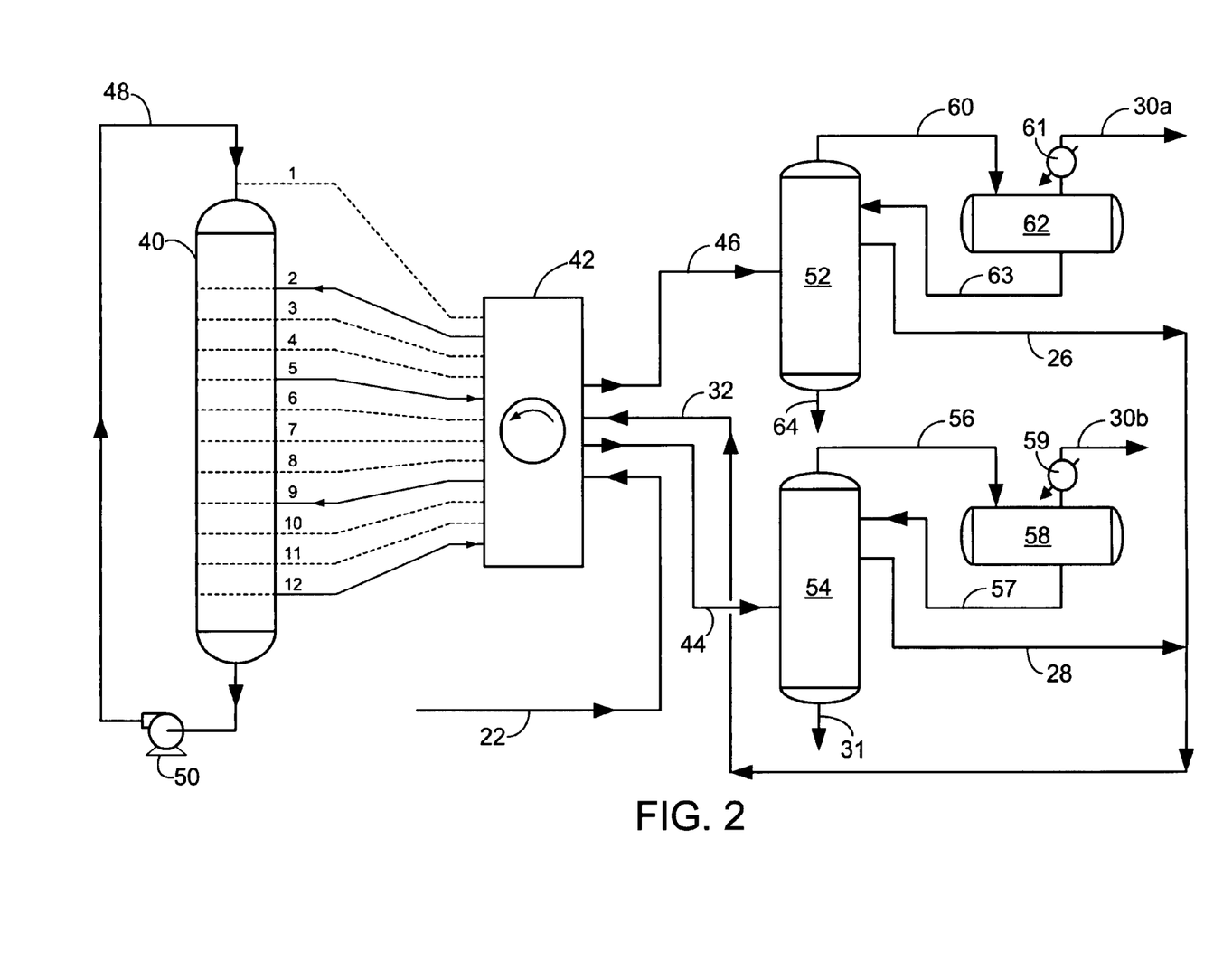
FIG. 2 is a schematic drawing of the of invention.

The flash drum bottoms 25 is passed to an adsorptive separation zone 24, which is as described in detail above. One mode of operation of adsorptive separation zone 24 is a simulated moving bed, however, for ease of understanding, FIG. 1 shows a simplified adsorptive separation zone 24 which contains a simulated moving bed and a raffinate column and receiver and an extract column and receiver. A more detailed drawing of the adsorptive separation zone is shown in FIG. 2. The simulated moving bed of adsorptive separation zone 24 normally runs at a pressure of from 1379 to 2172 kPa (abs) (200 to 315 psia). Desorbent stream 32 provides desorbent to adsorptive separation zone 24. Extract stream 64 removed from adsorptive separation zone 24 will contain normal paraffins, specifically normal pentane and normal hexane. Raffinate stream 31 removed from adsorptive separation zone 24 will contain isomerization products such as methylpentane, 2-methylpentane, 3-methylpentane, methylcyclopentane, cyclohexane, isopentane, 2,2,-dimethylbutane, 2,3-dimethylbutane, $C_7^+$ and other trace compounds. Light ends stream 30 removed from adsorptive separation zone 24 will contain propane, ethane, methane, hydrogen and other light gasses. The extract stream in line 64 is recycled to isomerization zone 14 by combining extract stream 64 with feed stream 13. The normal alkanes in the extract stream may be isomerized in isomerization zone 14 to produce more isomerized products.

As shown in FIG. 2, adsorptive separation zone 24 contains the simulated moving bed and rotary valve, two fractionation columns and two receivers. Referring now to the adsorptive separation zone 24 as illustrated in FIG. 2, distribution lines 1-12 are available to conduct fluid streams to or from the chamber 40 which houses twelve sub-beds of adsorbent. The distribution lines connect with the simulated moving bed at locations between successive sub-beds and separate the simulated moving bed into zones as described earlier. The distribution lines 1-12 are also connected to a rotary valve 42. Rotary valve 42 is further connected to: line 22 which conducts the mixture to be separated, the product separator effluent, described above, to the valve; line 44 which conducts raffinate containing the 2,2-dimethylbutane and the 2,3-dimethylbutane, and other branched alkanes away from the valve; line 32 which conducts the desorbent, n-butane, to the valve; line 46 which conducts the extract, normal alkanes, away from the valve. Each of lines 22, 32, 44, and 46 are equipped with a flow rate sensor and flow control valve (not shown). Line 48 conducts the effluent, or pumparound stream, from the bottom of chamber 40 back to the top of chamber 40 and is equipped with a pump 50.

The flow rates of each of the lines 22, 32, 44, and 46 and the step time of rotary valve 42 may be first set to selected values based on the operator's experience. The starting position of the rotary valve is not important; for this illustration the starting position of the rotary valve is such that the normal butane desorbent is directed to chamber 40 through distribution line 2, the extract containing normal alkanes is directed from chamber 40 through distribution line 5, the mixture to be separated, the product separator effluent, is directed to chamber 40 through distribution line 9, and the raffinate containing mono- and multimethyl-branched alkanes is directed from chamber 40 through distribution line 12. When the step time has elapsed, rotary valve 42 advances one index and now directs the normal butane desorbent through distribution line 3, the extract containing normal alkanes through distribution line 6, the mixture to be separated through distribution line 10, and the raffinate through distribution line 1. Both the extract and the raffinate will also contain lighter material not removed in the product separator, such as butanes, propane, methane, ethane and hydrogen. These materials would ordinarily be removed in a stabilizer, but the present invention eliminates the costly stabilizer and provides for the removal of these materials in the adsorptive separation zone. When the step time has again elapsed, the streams will again be directed to the next successive distribution line in the direction of the flow, and the continued progression of the streams will simulate the movement of the solid bed in the countercurrent direction.

When the mixture to be separated, conducted in distribution line 9, enters the simulated moving bed chamber 40 and contacts the adsorbent, the monomethyl-branched alkanes, which are only weakly adsorbed by the adsorbent and the multimethyl-branched alkanes, which are relatively unabsorbed by the adsorbent, are carried with the fluid flow and withdrawn from the bed in the raffinate stream conducted in distribution line 12. The normal alkanes which are strongly adsorbed by the adsorbent are carried with the solid bed in its countercurrent simulated movement thereby being separated from the multimethyl-branched alkanes. The normal alkanes are desorbed by the normal butane desorbent that is conducted to the bed through distribution line 2. The desorbed normal alkanes are removed from the bed in an extract stream through distribution line 5. Both the extract and the raffinate will also contain the light ends that would have traditionally been removed by a stabilizer.

The separated mono- and multimethyl branched alkanes in a mixture with desorbent, such as n-butane, and some light ends are conducted from rotary valve 42 in line 44 to a 20 to 200 or 20 to 50 equilibrium stage raffinate fractionator 54 operating at from 345 to 3551 kPa (abs) (50 to 515 psia) and temperatures of 66 to 93° C. (150 to 200° F.) at the top and 121 to 177° C. (250 to 350° F.) at the bottom. The $C_5$ and heavier branched alkanes are fractionated from the desorbent and lighter materials into the product raffinate stream 31. The portion with the lowest boiling point materials, any hydrogen, other gasses, and propane and lighter hydrocarbons are fractionated into raffinate fractionator overhead 56. It is expected that raffinate fractionator overhead 56 will also contain some n-butane desorbent. Raffinate fractionator overhead 56 is passed to raffinate receiver 58 where hydrogen and $C_3$ and lighter boiling material including gasses are removed in raffinate receiver overhead 30b which may be equipped with an optional chiller 59 to aid in preventing butane from being removed in raffinate receiver overhead 30b. Butane desorbent that may be present in raffinate fractionator overhead 56 separates into raffinate receiver bottoms 57 and is recycled to raffinate fractionator 54. N-butane desorbent is withdrawn from raffinate fractionator 54 in side draw stream 28 and is recycled to combine with desorbent in line 32 for use again in column 40.

The separated normal alkanes in a mixture with normal butane desorbent and light ends are conducted from rotary valve 42 in line 46 to a 20 to 200 or 20 to 50 equilibrium stage extract fractionator 52 operating at from 345 to 3551 kPa (abs) (50 to 515 psia) and temperatures of 66° to 93° C. (150° to 200° F.) at the top and 121° to 177° C. (250° to 350° F.) at the bottom. The $C_5$ and heavier normal alkanes are fractionated from the desorbent and lighter materials into the product extract stream 64. Product extract stream 64 may be recycled to combine with feed stream 13 and conducted to isomerization zone 14. The portion with the lowest boiling point materials, any hydrogen, other gasses, and propane and lighter hydrocarbons are fractionated into extract fractionator overhead 60. It is expected that extract fractionator overhead 60 will also contain some n-butane desorbent. Extract fractionator overhead 60 is passed to extract receiver 62 where hydrogen and $C_3$ and lighter boiling material including gasses are removed in extract receiver overhead 30a which may be equipped with an optional chiller 61 to aid in preventing butane from being removed in extract receiver overhead 30a. N-butane desorbent that may be present in extract fractionator overhead 60 separates into extract receiver bottoms 63 and is recycled to extract fractionator 52. N-butane desorbent is withdrawn from extract fractionator 52 in side draw stream 26 and is recycled to combine with desorbent in line 32 for use again in column 40. Extract receiver overhead 30a and raffinate receiver overhead 30b may be combined to form light ends stream 30 of FIG. 1.

What is claimed is:

1. A process for the isomerization of a feedstream comprising $C_5$ to $C_6$ hydrocarbons said process comprising:
    charging hydrogen and a feedstream comprising at least normal $C_5$ to $C_6$ hydrocarbons into an isomerization zone and contacting said hydrogen and feedstream with a solid acid isomerization catalyst at isomerization conditions to increase the branching of the feedstream hydrocarbons and produce an isomerization effluent stream comprising at least hydrogen, normal alkanes, branched alkanes, and light ends;
    passing the isomerization effluent stream to a product separator zone to separate a product separator zone overhead stream containing hydrogen from a product separator zone effluent containing the remainder of the isomerization effluent stream;
    passing the product separator zone effluent to a flash drum to separate a flash drum overhead stream containing light ends from a flash drum bottoms stream containing the remainder of the product separator zone effluent; and
    passing the flash drum bottoms stream to an adsorptive separation zone to separate three streams, a light ends stream comprising at least light ends, an raffinate stream comprising at least branched alkanes, an extract stream comprising at least normal alkanes.

2. The process of claim 1 further comprising recycling the extract stream to the isomerization zone.

3. The process of claim 1 wherein the catalyst is zeolitic.

4. The process of claim 1 wherein the catalyst is sulfated zirconia.

5. The process of claim 1 wherein the catalyst comprises a support comprising a sulfated oxide or hydroxide of at least an element of Group IVB (IUPAC 4) of the Periodic Table, a first component selected from the group consisting of at least one lanthanide series element mixtures thereof, and yttrium, and a second components selected from the group consisting of platinum, palladium, ruthenium, rhodium, iridium, osmium and mixtures thereof.

6. The process of claim 1 wherein said adsorptive separation zone is operated under liquid phase conditions.

7. The process of claim 1 further comprising blending said raffinate stream into a gasoline pool to produce a motor fuel.

8. The process of claim 1 wherein said feedstream includes $C_7$ and higher boiling hydrocarbons.

9. The process of claim 1 wherein said reaction zone includes a series of two reactors, the feed stream first enters a reactor operating at a temperature in the range of 120° to 225° C. and said effluent is recovered from a reactor operating at a temperature in the range of 60° to 160° C.

10. The process of claim 1 wherein the adsorptive separation zone is a simulated moving bed.

11. The process of claim 1 wherein the adsorptive separation zone contains solid adsorbent particles selected from the group consisting of silicalite, ferrierite, zeolite Beta, MAPO-31, SAPO-31, SAPO-11, and X-type zeolites ion exchanged with alkaline and alkaline earth cations, said particles having the selectivity normal alkanes>branched alkanes.

12. The process of claim 1 wherein the adsorptive separation zone uses a desorbent selected from alkanes having from 4 to 6 carbon atoms.

13. The process of claim 12 wherein the adsorptive separation zone comprises a at least four operationally distinct beds of adsorbent and said beds are operated in a simulated moving bed mode, a rotary valve, two fractionation columns and two receivers.

14. The process of claim 13 further comprising removing a simulated moving bed extract and a simulated moving bed raffinate from the simulated moving bed; passing the simulated moving bed raffinate to a raffinate fractionation column to separate a light ends stream, a desorbent stream and a raffinate fractionation column bottoms stream comprising branched alkanes; and passing the simulated moving bed extract to an extract fractionation column to separate a light ends stream, a desorbent stream and an extract fractionation column bottoms stream comprising normal alkanes.

15. The process of claim 14 further comprising recycling the desorbent streams from the extract and raffinate fractionation columns to the simulated moving bed.

16. The process of claim 14 further comprising passing the raffinate column light ends stream to a raffinate receiver to separate the desorbent from light ends; and passing the extract column light ends stream to an extract receiver to separate desorbent from the light ends.

17. The process of claim 14 further comprising recycling the extract fractionation column bottoms stream to the isomerization zone.

18. The process of claim 14 further comprising blending the raffinate column bottoms stream into a gasoline pool to produce a motor fuel.

19. The process of claim 14 wherein the raffinate fractionation column and the extract fractionation column are operated at from 345 to 3551 kPa (abs) (50 to 515 psia) and temperatures of 66° to 93° C. (150° to 200° F.) at the tops and 121° to 177° C. (250° to 350° F.) at the bottoms.

20. The process of claim 1 wherein the adsorptive separation zone contains a simulated moving bed operated at from 1379 to 2172 kPa (abs) (200 to 315 psia), the product separator zone is operated at from 689 to 4137 kPa (abs) (100 to 600 psia), and the flash drum is operated at from 0 to 148 kPa (abs) (0 to 215 psia).

* * * * *